United States Patent [19]

Beaudenon et al.

[11] Patent Number: 5,411,857
[45] Date of Patent: May 2, 1995

[54] PROBES FOR PAPILLOMAVIRUSES AND AN IN VITRO DIAGNOSTIC PROCEDURE FOR PAPILLOMA INFECTIONS

[75] Inventors: Sylvie Beaudenon, Clamart; Dina Kremsdorf; Odile Croissant, both of Paris; Gérard Orth, Sceaux, all of France

[73] Assignees: Institut Nationale de la Sante; Institut Pasteur, both of Paris, France

[21] Appl. No.: 914,005

[22] Filed: Jul. 16, 1992

Related U.S. Application Data

[63] Continuation of Ser. No. 714,347, Jun. 12, 1991, abandoned, which is a continuation of Ser. No. 584,397, Sep. 13, 1990, abandoned, which is a continuation of Ser. No. 453,219, Dec. 21, 1989, abandoned, which is a continuation of Ser. No. 275,953, Nov. 25, 1988, abandoned, which is a continuation of Ser. No. 8,003, Jan. 29, 1987, abandoned, which is a continuation-in-part of Ser. No. 760,993, Jul. 31, 1985, abandoned.

[30] Foreign Application Priority Data

Jan. 31, 1986 [FR] France ................. 86 01425

[51] Int. Cl.⁶ .......................... C12Q 1/70; C12Q 1/68
[52] U.S. Cl. ........................... 435/5; 435/6; 536/23.72
[58] Field of Search .............. 435/5, 6, 810; 436/808; 935/78; 536/23.72

[56] References Cited

U.S. PATENT DOCUMENTS 4,358,535 11/1982 Falkow et al. .
4,419,446 12/1983 Howley et al. .
4,551,270 11/1985 Danos et al. .

FOREIGN PATENT DOCUMENTS

0489442A1 6/1991 European Pat. Off. .

OTHER PUBLICATIONS

Gissman, L. et al., Proc. Nat'l. Acad. Sci. 80: 560–563 (1983).
Suggs, S. V. et al., Proc. Nat'l. Acad. Sci. 78:6613–6617 (1981).
European Patent Application No. 90120403.2, Lancaster, W. D. et al., "Use of Conserved Nucleotide Primers to Amplify Human Papillomavirus DNA Sequences," Publication No. 0 425 995 A2, published May 8, 1991.
International Patent Application No. PCT/US90/07075, filed Dec. 3, 1990, Hendricks, D. A. et al., "Detection of HPV Transcripts," Publication No. WO91/08312, published Jun. 13, 1991.
Chem. Abst. vol. 99, No. 3, issued Dec. 5, 1983, p. 218, 188882k, Lancaster, W. D. et al. "Human Papillomavirus . . . Uterine Cervix".
Rando, R. F. et al, J. Virol 57 Jan. 1986, pp. 353–356.
Danos, O. et al., EMBO 1 1982, pp. 231–236.
Schwarz, E. et al., EMBO 2 1983, pp. 2341–2348.
Howley, P. Arch. Pathol. Lab. Med. 106 1982, pp. 429–432.
Chen. E. Y. et al, Nature 299, 1982, pp. 529–534.
Rio, G. et al, C.R. Acad. Sci. Ser. III 14, 1984, pp. 575–580.
Pfister, H. Rev. Biochem. Pharm. 99, 1983, pp. 111–181.

*Primary Examiner*—Amelia Burgess Yarbrough
*Attorney, Agent, or Firm*—Finnegan, Henderson, Farabow, Garrett & Dunner

[57] ABSTRACT

The invention relates to papillomaviruses, particularly to DNA-HPVs isolated from the papillomaviruses IP5 and IP6, the restriction maps of which are presented in FIGS. 10 and 11, and also to probes containing these DNA-HPVs or fragments obtained from them. The invention relates, in addition, to "kits" containing distinct groups of probes, containing one of these DNA-HPVs or DNA-HPV fragments, as well as a procedure for the detection and identification of papillomaviruses which makes use of these different probes.

8 Claims, 11 Drawing Sheets

PROBES FOR PAPILLOMAVIRUSES AND AN IN VITRO DIAGNOSTIC PROCEDURE FOR PAPILLOMA INFECTIONS

CROSS-REFERENCE TO RELATED APPLICATION

This application is a continuation of application Ser. No. 07/714,347, filed Jun. 12, 1991, now abandoned, which is a continuation of application Ser. No. 07/584,397, filed Sep. 13, 1990, now abandoned, which was a continuation of application Ser. No. 07/453,219, filed Dec. 21, 1989, now abandoned, which was a continuation of application Ser. No. 275,953, filed Nov. 25, 1988, now abandoned, which was a continuation of application Ser. No. 008,003, filed Jan. 29, 1987, now abandoned, which was a continuation-in-part of application Ser. No. 760,993, filed Jul. 31, 1985, now abandoned.

BACKGROUND OF THE INVENTION

The invention relates to the DNAs of papillomaviruses, and more particularly to the probes derived from these papillomaviruses, as well as procedures for their implementation in the in vitro diagnosis of papillomavirus infections.

The expression "papillomavirus" covers a large number of viruses, which have in common the property of being held responsible for several forms of viral infection extending from relatively benign epidermal and mucosal warts to hyperplasias liable to degenerate into intra-epithelial neoplasias and cancers of the skin and mucous membranes. Of these papilloma infections, mention will also be made more especially of epidermodysplasia verruciformis, which will sometimes be designated below by the expression "EV".

Quite a number of types of papillomavirus have already been described. The European patent application No. 85. 402362.9-2105, filed on Nov. 29, 1985, and published on Sep. 10, 1986, as No. 0192001, describes quite a number of new types and subtypes of papillomaviruses which were isolated from warts and macular lesions liable to give rise to the development of skin cancer in a high proportion of those patients affected and from pre-cancerous lesions of the skin, and lesions in oral hyperplasia and in a cancer of the uterine cervix.

The major role of various types of human papillomaviruses (HPV) in the genesis of neoplasia is an accepted fact. Their pathogenicity is also influenced by various genetic factors, and in particular immune and-/or extrinsic factors such as actinic radiation.

Several new types and subtypes of papillomaviruses were identified in the previous application. The use in more refined in vitro diagnostic techniques of the DNAs of these new papillomaviruses, used individually or in combination with each other and/or with the DNAs of previously known HPVs has also been described in this application.

The general observation was made in the European application that papillomaviruses, although differing very much among themselves, have sizes of the order of 7,000–8,000 base pairs. Furthermore, their genomes may present certain degrees of homology, assessed as percentages of homology between types and subtypes of papillomaviruses in hybridization assays carried out under so-called non-stringent conditions or also under stringent hybridization conditions.

It has been said that the papillomaviruses which present percentages of homology of less than 50% under stringent conditions belong to different types. Viruses for which percentages of homology higher than 50% are observed under the same stringent conditions are believed to belong to the same type.

The hybridization assays under non-stringent conditions involve placing in mutual contact DNAs derived from two isolates of virus under the conditions described by HEILMAN, C. A. et al. 1980, J. Virol., 36, 395–407, and CROISSANT et al., 1982, C. R. Acad. Sci. Paris, 294, 581–586 (heteroduplex molecules).

Performance of hybridization assays under stringent conditions involves placing in mutual contact DNAs derived from two isolates of virus under the conditions described by HEILMAN, C. A. et al., 1980, and KREMSDORF, D. et al. ((1982), J. Virol. 43, 436–447 and 1983, J. Virol., 48, 340–351) and DAVIS, R. W. et al., 1971, Methods Enzymol., 21, 413–418 heteroduplex molecules).

Based on these considerations, several new viruses were described in the previous application. Similarly, genetic recombinants have been described containing all or part of the genomes of these viruses (designated DNA-HPVs). The invention of the previous application consequently related to each of the DNA-HPVs chosen from among the totality of DNAs which were of a molecular size ranging from 7,000 to 8,000 base pairs and which were characterized by restriction maps which are presented in the figures also reproduced in this application and which related more particularly to the DNA-HPVs obtained from papillomaviruses and which are designated HPV2d, HPV10b, HPV14a, HPV14b, HPV15, HPV17a, HPV17a, HPV17b, HPV19, HPV20, HPV21, HPV22, HPV23, HPV24, HPV28, HPV29, HPV31, HPV32, HPV-IP2 and HPV-IP4.

The invention of the previous application also related to mixtures or "cocktails" of DNA-HPVs isolated from the new papillomaviruses or from ones already known at the time of the filing date of the previous application, or hybridization probes containing them and which may be put to use for the more effective diagnosis of various classes of infections, and even for the diagnosis of the level of risk which accompanies the discovery in a patient of specific papillomaviruses. The number of the probes for papillomaviruses described in the previous application, to which are added those constituted from the genomic DNAs of papillomaviruses which had already been isolated and their combinations in defined mixtures, thus makes it possible to perform more refined diagnoses, in particular, by enabling a clear distinction to be made between the various classes of infection and the various types of papillomavirus to which they may be ascribed, or the infections which are liable to develop as a result of the influence of such papillomaviruses and, within a given class of specific infections, by providing a better diagnosis of the degree of risk of these infections being transformed into more serious diseases. In particular, the invention of the previous application furnished reagents which make it possible, in cases of infections manifesting themselves as cases of epidermodysplasia verruciformis, to assess more precisely the degree of risk that the latter will develop into epidermal cancers.

Therefore, the invention of the previous application related more particularly to diagnostic mixtures; a group of preferred mixtures was defined as containing:

1) at least the DNA of HPV2d,
2) at least one of the DNAs of HPV10b, 28 and 29,
3) at least one of the DNAs of HPV17, 24,
4) at least one of the DNAs of HPV14, 15, 17, 19, 20, 21, 22, 23 and IP4,
5) at least one of the DNAs of HPV15 and 17,
6) the DNA of HPV24,
7) the DNA of HPV14, 32 and IP4,
8) the DNA of HPV31,
9) the DNA of HPV32,
10) at least one of the DNAs of HPV16, 18 and IP2,
it being understood that the DNAs of the ten groups were chosen so that the groups were different from each other under all circumstances.

In group 10), the DNA of hPV-IP2 is preferably associated with the DNA of HPV16 or HPV18.

The restriction maps of the DNA-HPVs concerned are presented in the FIGS. 1 to 10 of the appendices.

The restriction maps give the positions of the cleavage sites of various restriction endonucleases. The origin of a map is generally constituted by a unique cleavage site. The distances from the origin are expressed as percentages of the length of the genome.

SUMMARY OF THE INVENTION

The present invention relates to recently isolated papillomaviruses, the genomic DNAs which can be extracted from them or fragments of these genomic DNAs, as well as new hybridization probes which can be formed from these DNA-HPVs of their fragments.

The invention also relates to a procedure for the preparation of a DNA-HPV probe, characterized by the cloning of a vector in an appropriate host, this vector having been subjected to prior modification by in vitro recombination of all or part of the DNA of a virus chosen from HPV-IP5 and HPV-IP6 and a suitable vector to produce a DNA recombinant containing this DNA at a site in the vector permitting its cloning in the host, particularly in a bacterium, and by the recovery and purification of the cloned recombinant DNA. Advantageously, the vector used is a plasmid or a phage capable of being replicated in a procaryotic microorganism, such as *E. coli*.

This DNA-HPV probe is also preferably labelled to make it more convenient to use. Use may be made of any principle of labelling, such as radioactivity, immunofluorescence, enzyme activity etc.

The invention also relates to new "cocktails" of probes containing them or to their use in the "cocktails" of probes already described in the previous application, but supplemented with one or other of the DNA-HPVs which are the subject of the present application and, by extension, to even more sophisticated diagnostic "kits".

The DNA-HPVs according to the present invention are characterized by the restriction maps presented in FIGS. 10 and 11 and designated HPV-IP5 and HPV-IP6, respectively.

The hybridization probes constructed from the genome of HPV-IP5 or the genome of HPV-IP6 are particularly useful for diagnosis and/or screening in vitro, under the conditions which were described in the previous application and which will be described again later, of the types of papillomavirus which constitute a risk of developing into genital neoplasias and, in particular, into cancers of the uterine cervix. The hybridization probes are advantageously incorporated into diagnostic mixtures for diseases of the same type to which reference will be made again later.

The invention also relates to the aforementioned DNA-HPV fragments or to fragments capable of hybridizing with these latter, in particular, under stringent conditions. Similarly, the invention relates to recombinant DNAs containing all or part of each of the DNA-HPVs cited above, and more especially to DNA recombinants containing fragments corresponding to the genes E1, E2, E6-E7, L1, L2 and to the intergenic region, NC, respectively, or fragments containing sequences corresponding to the intergenic regions of the said DNA-HPVs. The invention finally relates to the probes which can be constituted from these respective DNA-HPVs or from corresponding fragments, and the in vitro diagnostic procedures in which these probes are used.

The preparations of viral DNA were extracted according to the methods which will be described below in examples 1 and 2.

In what follows the conditions under which the viruses were isolated will be described in more detail, and will be followed by a description of the conditions under which the DNA-HPVs were obtained from these viruses.

BRIEF DESCRIPTION OF DRAWINGS

FIG. 1 depicts restriction maps of HPV1a, HPV2d, and HPV4a.

MOLECULAR CLONING AND CHARACTERIZATION OF A NOVEL TYPE OF HPV ASSOCIATED WITH GENITAL NEOPLASIAS AND CANCERS OF THE UTERINE CERVIX (HPV-IP5)

The presence of a novel type of HPV was demonstrated in the DNA extracted from biopsies of intraepithelial neoplasias (bowenoid papules of the penis) by Southern hybridizations under non-stringent conditions with a radioactive DNA probe specific for HPV6 or HPV10. The study of the sensitivity of the DNA of that HPV to several restriction endonucleases has shown that the enzyme EcoRI cleaves the viral DNA once. After digestion of the DNA extracted from lesions by the enzyme EcoRI, the fraction containing molecules of DNA of 8 kb was purified by centrifugation in a sucrose gradient. The DNA molecules of 8 kb were inserted at the EcoRI site into the DNA of the bacteriophage λgtWES B. After encapsidation of the recombinant DNA and the infection of bacteria *Escherichia coli* K12 (strain LA101), the recombinant bacteriophages into which the DNA of the HPV had been integrated were selected by the technique of hybridization on bacteriophage λ plaques (Benton and Davis) by using a radioactive DNA probe specific for the DNA of HPV6 under non-stringent conditions. Several recombinant bacteriophages containing the totally of the viral sequences were isolated. The cleavage of the DNA of the recombinant bacteriophages by the restriction enzyme EcoRI gives rise to a fragment of 8 kb which hybridizes with the DNA of HPV6 under non-stringent conditions. The cleavage of the DNA of the recombinant bacteriophages and the preparation of the DNA extracted from lesions by a mixture of the endonucleases EcoRI and PstI gives rise to the same seven fragments, the total molecular weight of which corresponds to that of the genome of an HPV (8 kb).

Figure 1:
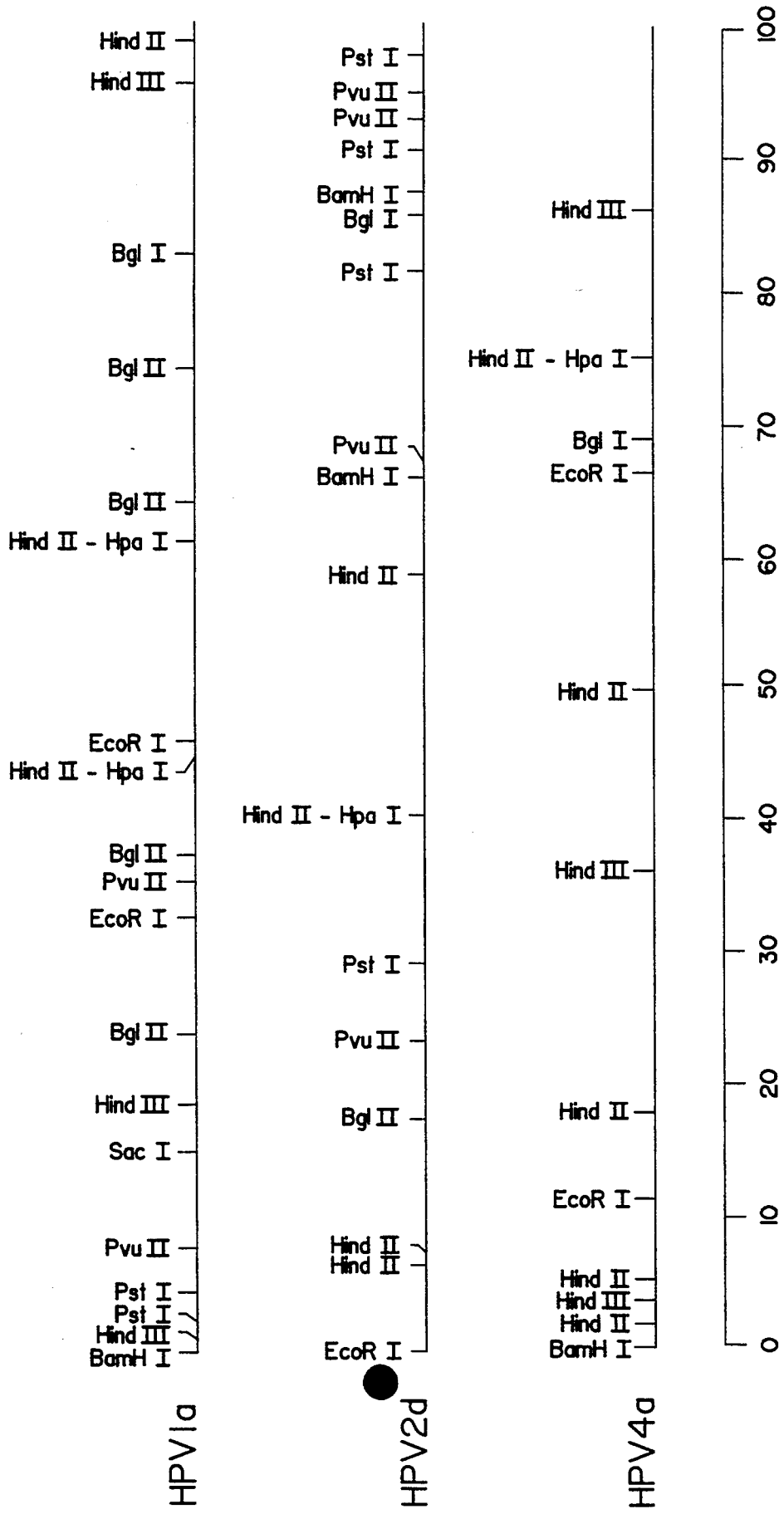
Figure 2:
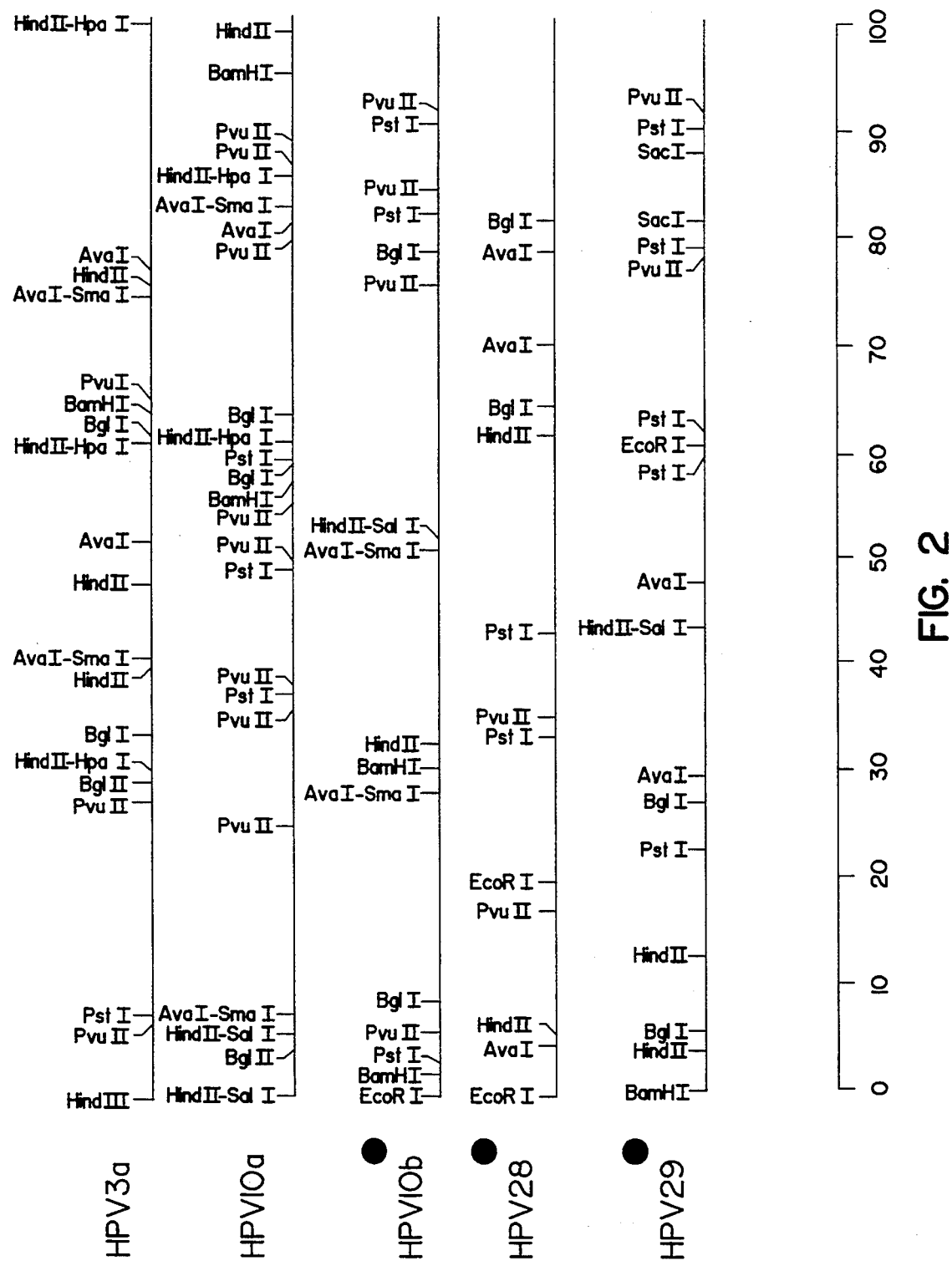
FIG. 2 depicts restriction maps of HPV3a, HPV10a, HPV10b, HPV28, and HPV29.
Figure 3:
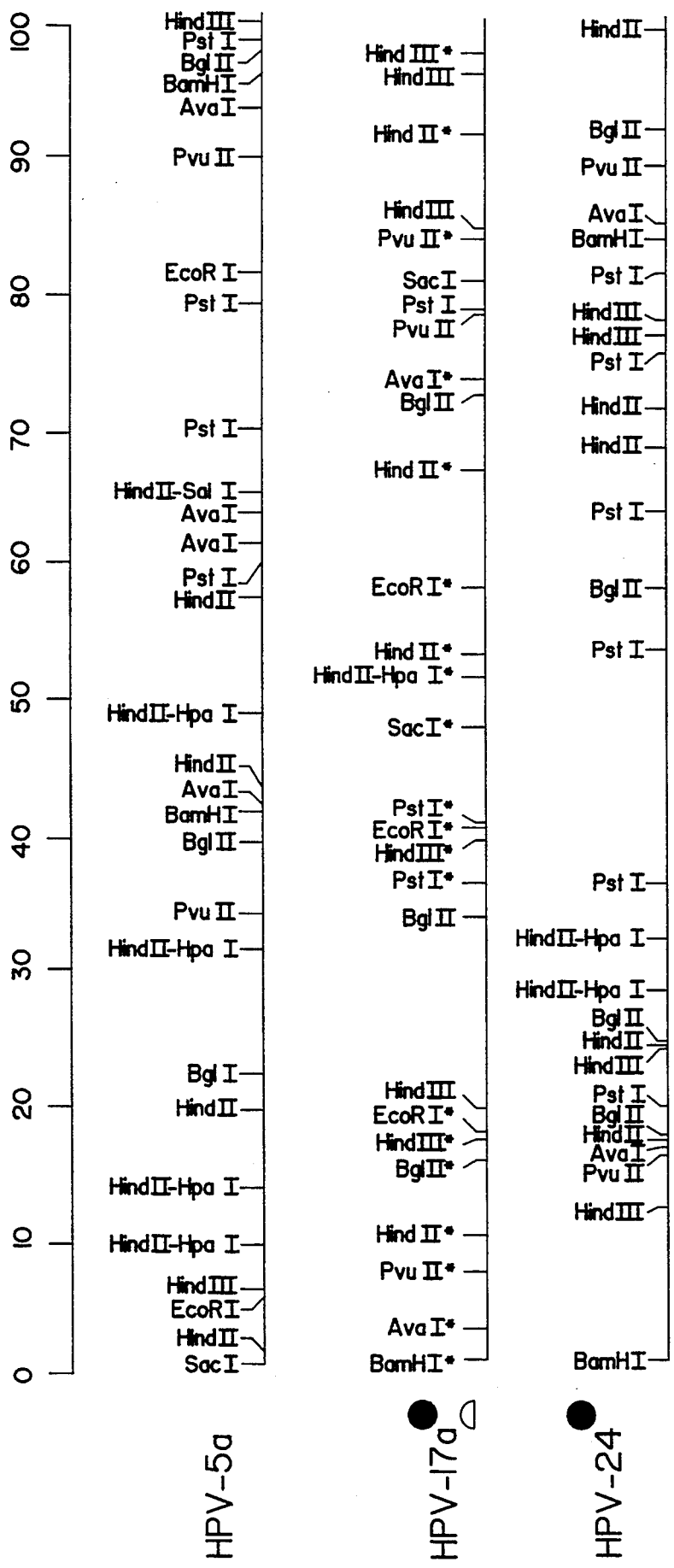
FIG. 3 depicts restriction maps of HPV5a, HPV17a, and HPV24.
Figure 4A:
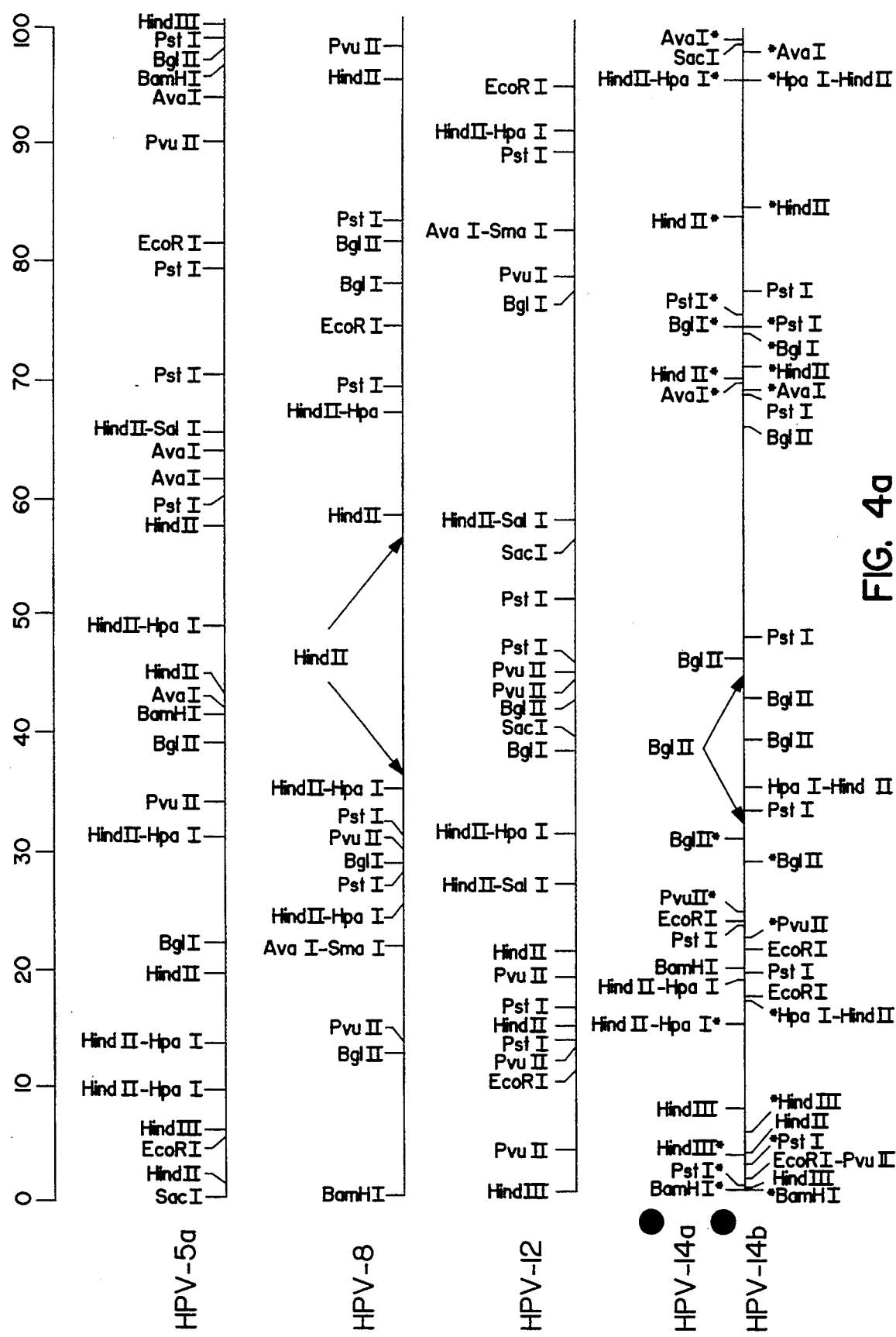
FIG. 4a depicts restriction maps of HPV5a, HPV8, HPV12, HPV14a, and HPV14b.
Figure 4B:
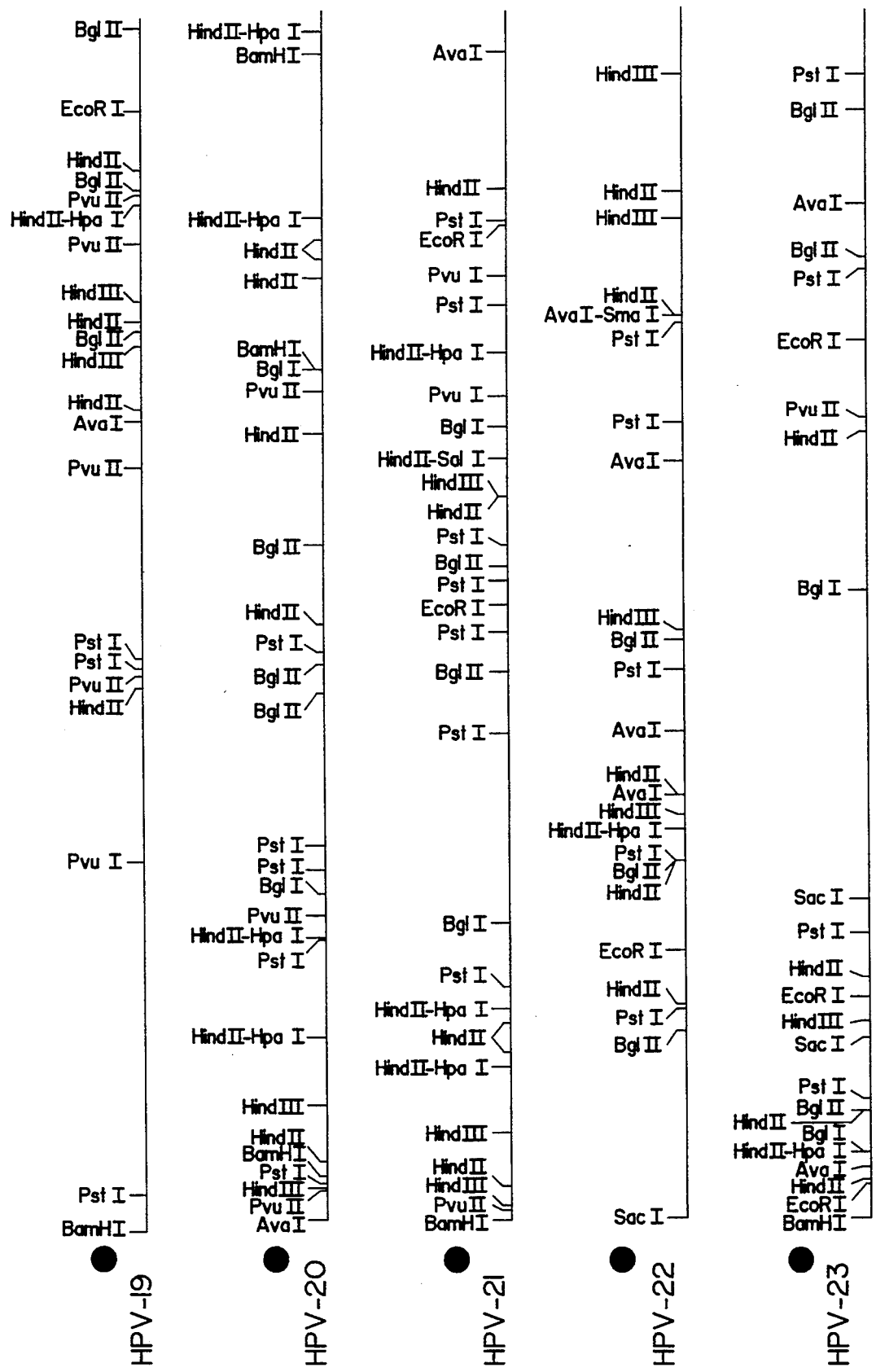
FIG. 4b depicts restriction maps of HPV19, HPV20, HPV21, HPV22, and HPV23.
Figure 5:
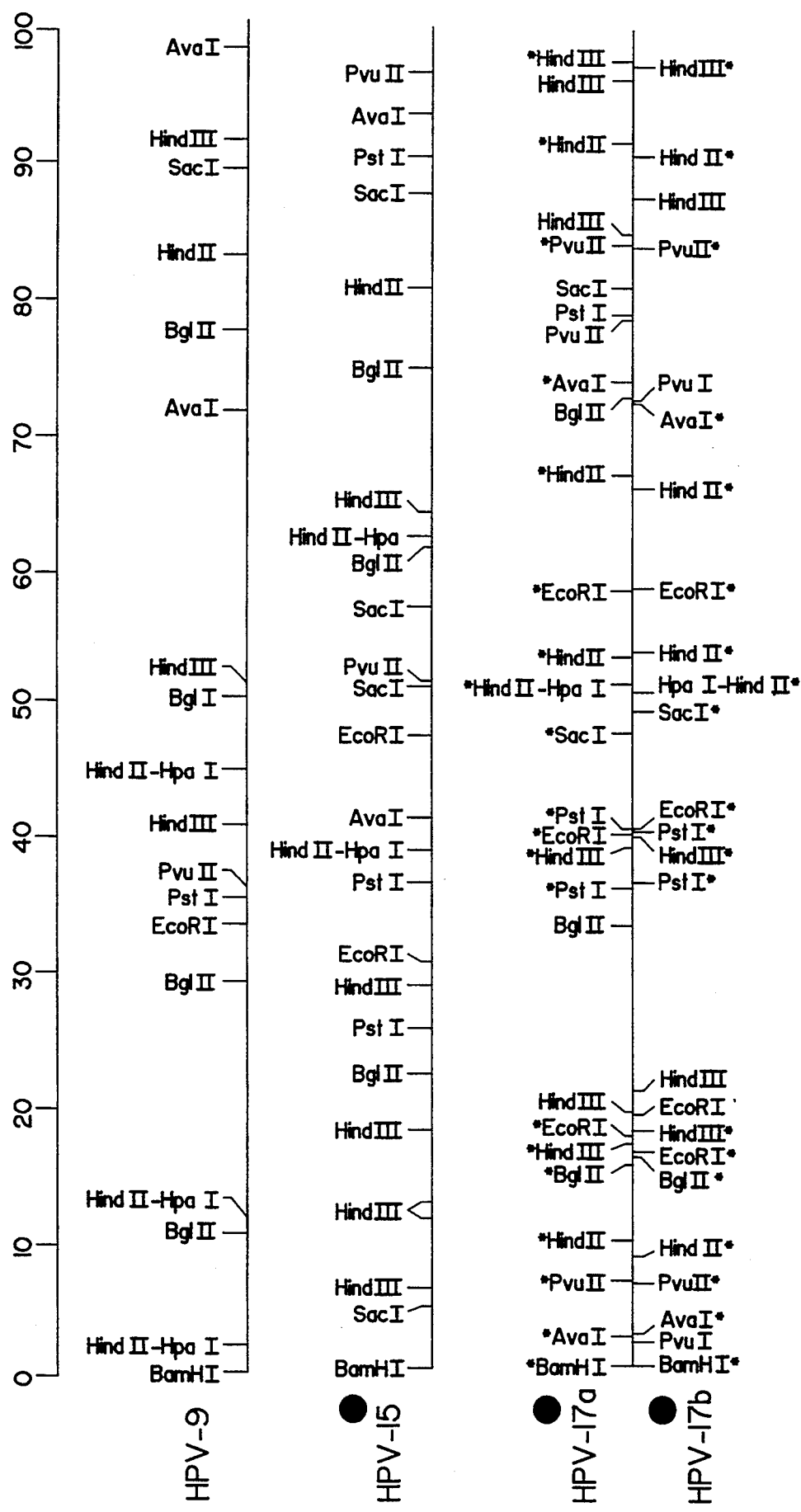
FIG. 5 depicts restriction maps of HPV9, HPV15, HPV17a, and HPV17b.
Figure 6:
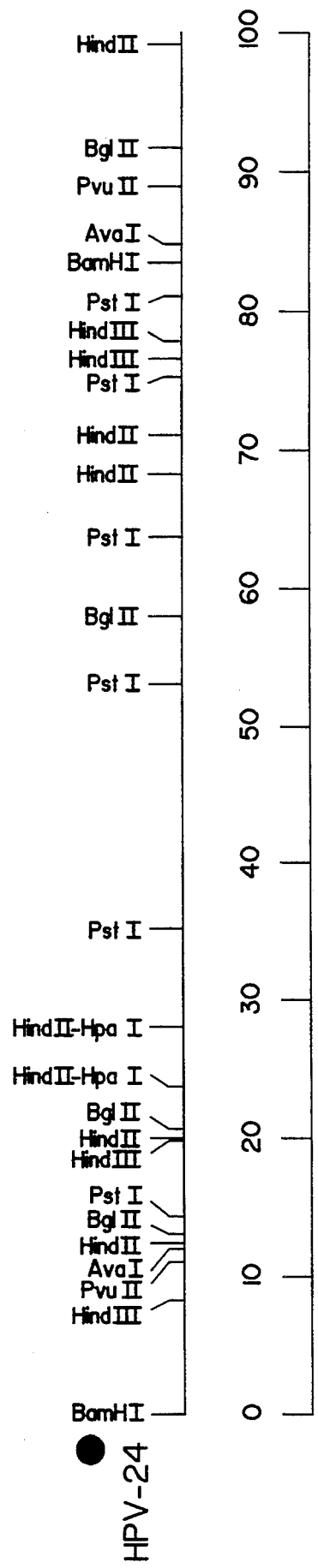
FIG. 6 depicts a restriction map of HPV24.
Figure 7:
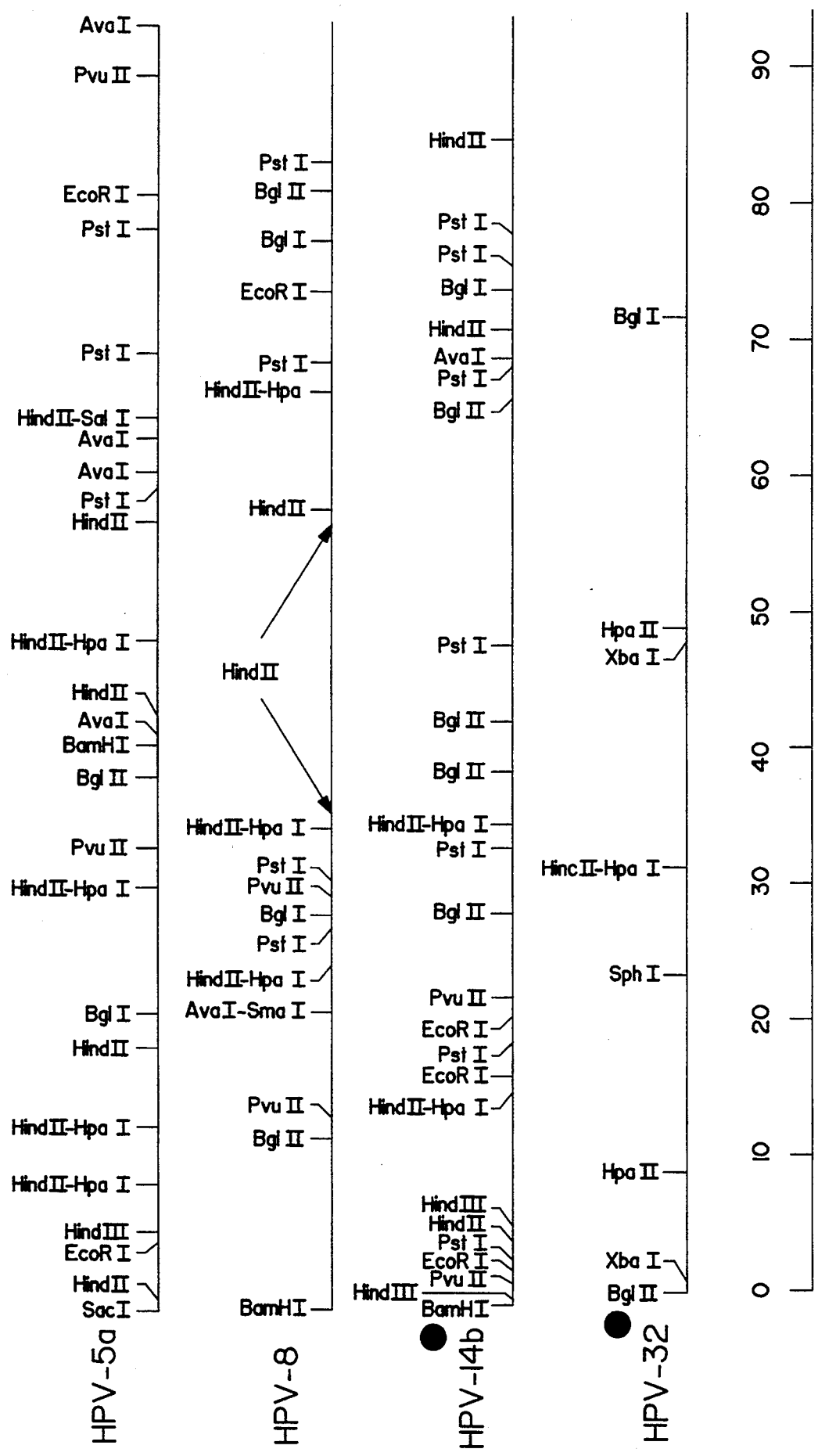
FIG. 7 depicts restriction maps of HPV5a, HPV8, HPV14b, and HPV32.
Figure 8:
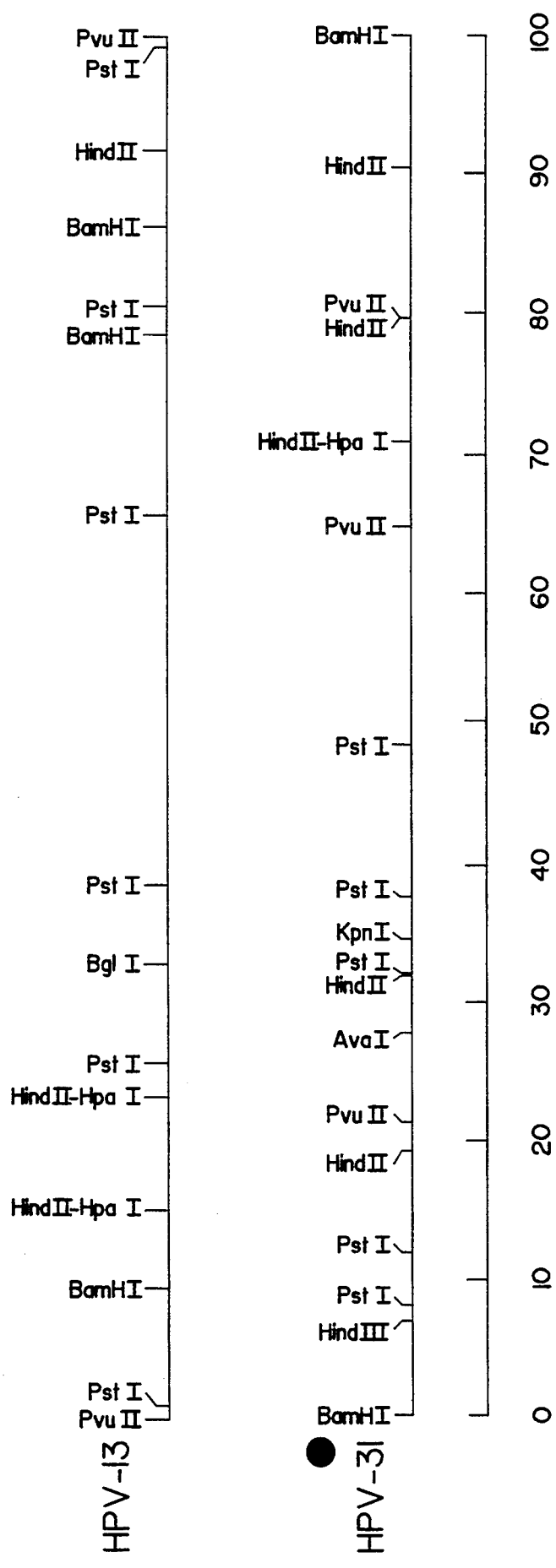
FIG. 8 depicts restriction maps of HPV13 and HPV31.
Figure 9:
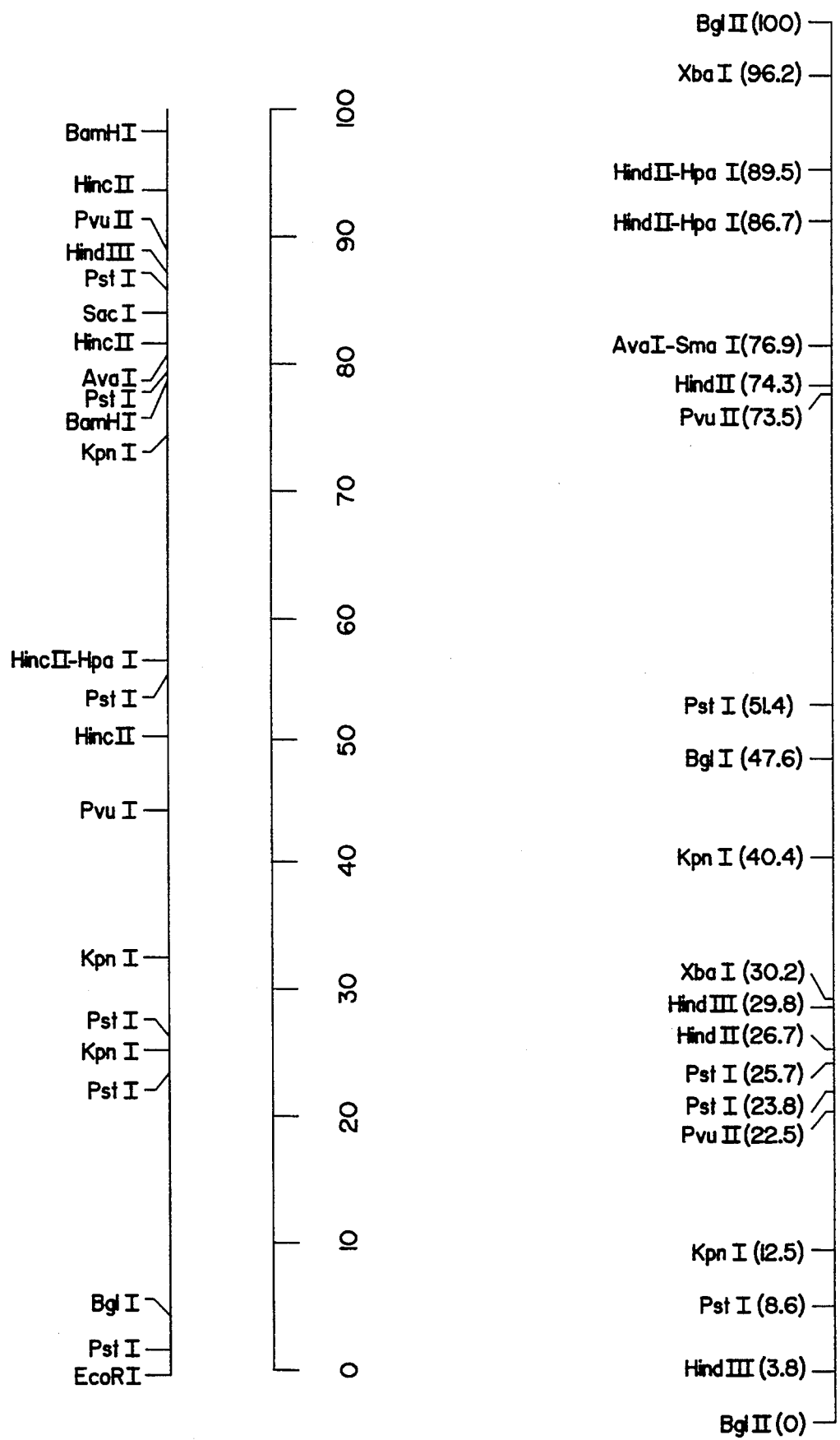
FIG. 9 depicts restriction maps of HPVIP4 and HPVIP2.
Figures 10, 11:
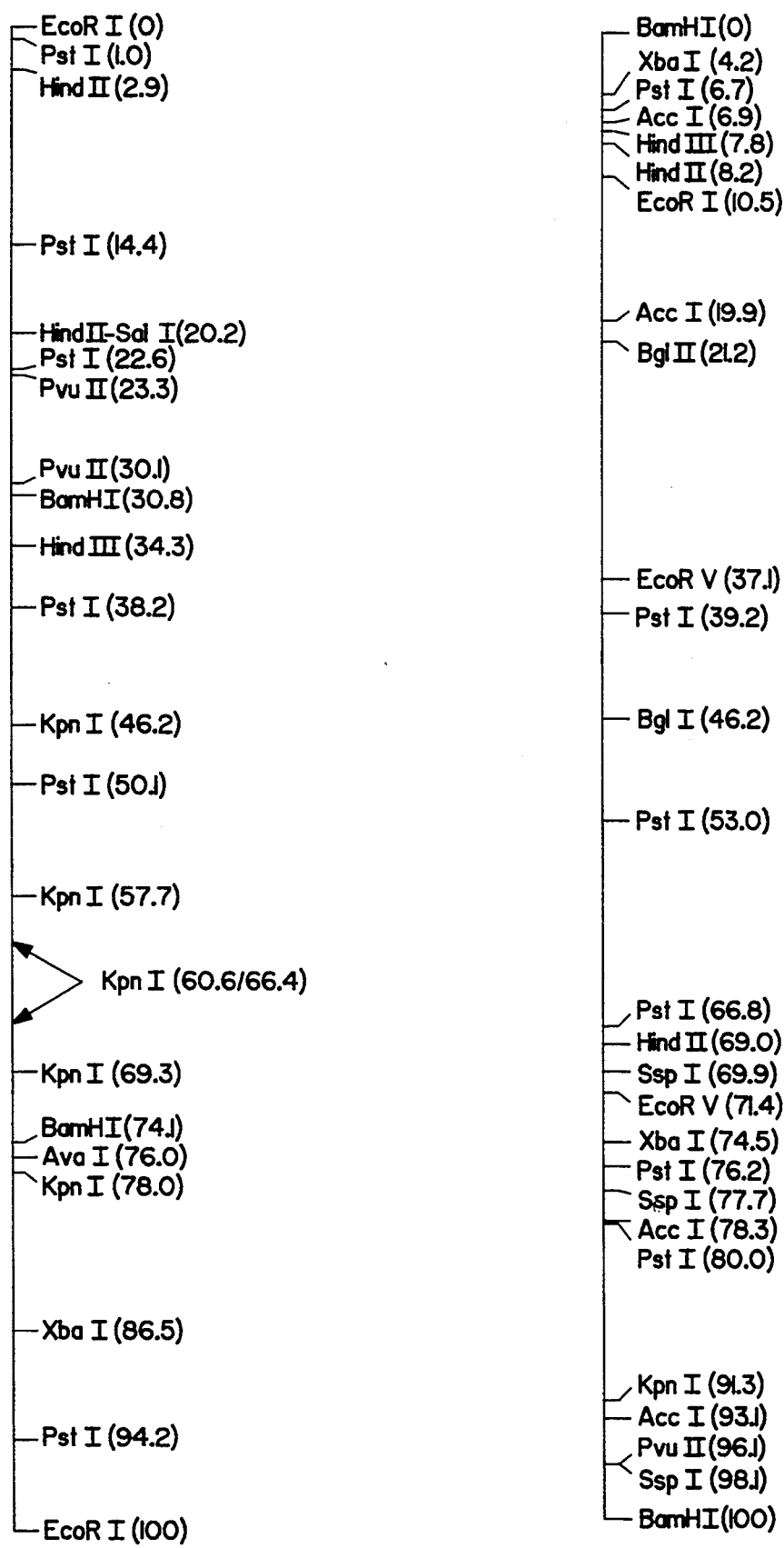
FIG. 10 depicts a restriction map of IP5.
FIG. 11 depicts a restriction map of IP6.

The DNA of the novel HPV was excised from the sequences of phage DNA and recloned in the plasmid pSP65. A restriction map of the viral DNA was constructed on the basis of a study of the sensitivity of this DNA to 16 restriction endonucleases. 22 cleavage sites were thus localized (Fig. 10). The restriction map of the novel HPV is different from that of all of the HPVs identified up to now. The degree of homology between the DNA of the novel HPV and the DNA of the previously known HPVs was analyzed in Southern hybridization experiments under stringent conditions by using a radioactive probe prepared from the DNA purified from the novel HPV. A partial homology was detected with the DNA of HPV18 and, to a lesser extent, with that of HPV26 and a low degree of homology was detected with the DNA of the HPV types 2, 6, 10, 13, 29, 31 and HPV-IP2. The degree of homology between the DNA of the novel HPV and the DNA of HPV18 was determined more precisely by means of DNA-DNA reassociation experiments in liquid medium, followed by treatment of the hybrids with nuclease S1. A degree of homology of 2% was detected between these two DNAs. The novel virus characterized from bowenoid papules of the penis thus constitutes a new type of HPV, provisionally designated HPV-IP5.

Electron microscopic studies of the heteroduplex molecules formed under different conditions between the DNA of HPV-IP5 and the DNA of HPV-16 has made it possible to align the maps of these two genomes and to define the theoretical positions of the different genes borne by the DNA of HPV-IP5 in relation to the origin of its DNA map. These positions are expressed as percentages of the length of the genome measured from this origin (point 0 on the restriction map shown in FIG. 10).

| Putative localization of the principal genes and the intergenic region (NC) of HPV-IP5 | |
| --- | --- |
| | IP5 |
| E6-E7 | 18–28 |
| E1 | 28–53 |
| E2 | 51.5–66 |
| L2 | 69.5–89 |
| L1 | 87–8 |
| NC | 7.5–18 |

The use of radioactive probes prepared from the purified DNA of HPV-IP5 has made it possible to determine the pathogenicity of this virus. In the course of a study of 1522 samples of cervico-vaginal cells, taken in an attempt to define more clearly the frequency of infection of the epithelium of the uterine cervix by a HPV, HPV-IP5 was detected in 5 of the 110 samples containing a HPV. Moreover, HPV-IP5 was detected in 3 of the 93 biopsies of invasive cancers of the uterine cervix which were analyzed. In these 3 cases, the integration of the totality of the DNA sequences of HPV-IP5 into the cellular DNA was observed.

HPV-IP5 thus constitutes a genital type of HPV, presenting oncogenic potential. It is therefore desirable to incorporate it into all of the mixtures of DNA from HPVs intended for the preparation of molecular probes, with a view to diagnosing or screening for HPV types constituting a risk of developing into genital neoplasias and, in particular, cancers of the uterine cervix.

Molecular cloning and characterization of a novel type of HPV associated with genital lesions (HPV-IP6)

The presence of another novel type of HPV was demonstrated in DNA extracted from vulval lesions described as papillomas showing minimal atypical cellular characteristics when hybridized under stringent conditions with a probe of radioactive DNA specific for HPV-31. A study of the sensitivity of the DNA of this HPV to several restriction enzymes has shown that the enzyme BamHI cleaves the viral DNA once. After digestion of the DNA extracted from lesions of BamHI, the DNA molecules of 8 kb were purified by centrifugation on a sucrose gradient, then inserted into the DNA of the bacteriophage lambda L 47.1 at the BamHI site. After encapsidation of the recombinant DNA and infection of bacteria *Escherichia coli* K12 (strain LA 101), the recombinant bacteriophages into which the DNA of the novel HPV had been integrated were selected by the technique of hybridization on bacteriophage λ plaques (Benton and Davis) by using a radioactive DNA probe specific for HPV31 under stringent conditions. Several recombinant bacteriophages containing the whole of the viral sequences were isolated. Cleavage of the DNA of the recombinant bacteriophages by the endonuclease BamHI gives rise a 8 kb fragment which hybridizes with the DNA of HPV31 under stringent conditions. The cleavage of the DNA of the recombinant bacteriophages and of the DNA prepared from lesions by a mixture of the endonucleases BamHI and PstI gives rise to the same 7 fragments, the total molecular weight of which corresponds to that of the papillomavirus genome.

The DNA of the novel HPV was excised from the sequence of phage DNA and recloned in the plasmid pSP64. A restriction map of the DNA was constructed on the basis of the study of the sensitivity of this DNA to 20 restriction endonucleases. In this way, 26 cleavage sites were localized (FIG. 10). This map is different from that of all other HPVs isolated to date. The degree of homology between the DNA of the novel HPV and the DNA of the HPV identified up to now was analyzed by Southern hybridizations under stringent conditions by using a radioactive probe of DNA specific for the novel HPV. Partial hybridization was observed with the DNA of HPV31 and a weak cross hybridization was obtained with the DNAs of HPV6 and 13 and HPV-IP2. A more precise determination of the homologies between the DNA of the novel HPV and the DNA of HPV31 was made by DNA-DNA reassociation in liquid medium, followed by treatment of the hybrids with nuclease S1. A hybridization of 20% was detected between the two DNAs. The virus isolated from vulval bowenoid papillomas thus constitute a new type of HPV, provisionally designated HPV-IP6.

Electron microscopic studies of the heteroduplex molecules formed under different conditions between the DNA of HPV-IP6 and the DNA of HPV31 has made it possible to align the maps of these two genomes and to define the theoretical positions of the different genes borne by the DNA of HPV-IP6 as indicated below and in relation to the origin of the map presented in FIG. 12 and expressed as percentages of the length of the genome measured from this origin.

| Putative localization of the principal genes and the intergenic region (NC) of HPV-IP6 | |
| --- | --- |
| | IP6 |
| E6-E7 | 11.5-21.5 |
| E1 | 21.5-46.5 |
| E2 | 45-59.5 |
| L2 | 63-82.5 |
| L1 | 80.5-15 |
| NC | 1.5-11.5 |

The use of radioactive probes prepared from the purified DNA of HPV-IP6 has made it possible to determine the pathogenicity of this virus.

Samples taken from benign proliferative lesions (condylomas, papillomas) or from intraepithelial neoplasias of the external genital organs or of the perianal region and from the uterine cervix in a total of 163 patients were analyzed. The DNA of HPV-IP6 was detected in 10 patients presenting benign lesions (condylomas, papillomas).

In the course of a study of 1522 samples of cervicovaginal cells, taken in an attempt to define more clearly the frequency of infection of the epithelium of the uterine cervix by a HPV, the DNA of HPV-IP6 was detected in 9 samples representing normal or inflammatory cytology or a mild dysplasia out of 110 samples containing a HPV DNA.

HPV-IP6 thus constitutes an additional type of genital HPV, which occurs relatively frequently and probably possesses only a low oncogenic potential. It is therefore desirable to incorporate it into all of the mixtures of DNA derived from HPVs intended for the preparation of molecular probes, with a view to diagnosing or screening for sexually transmitted types of HPV, agents of benign genital tumors not constituting a major risk of developing into genital neoplasias and, in particular, cancers of the uterine cervix.

Given the great diversity of HPVs likely to be isolated from various types of warts or other epidermal or mucosal lesions, it was nonetheless deemed preferable to make use of mixtures comprising more than one or two DNA-HPVs for the diagnosis of each type of disease mentioned in the Table, as soon as other DNA-HPVs were recognized as also being capable of playing a role in the same type of disease. The diagnosis of the type of infection and of its possible course will be rendered more efficacious, the larger the number of probes used. In addition, hybridization assays performed with different mixtures of probes will make possible differential diagnoses which would be expected to render more probable the correctness of the diagnosis of the disease from which the patient is suffering.

The invention thus also relates more particularly to mixtures or cocktails of different DNAs-HPVs (or probes containing these DNAs-HPVs or sequences of the latter) which can be used in combination for performing overall diagnoses of the different types of infections with papillomaviruses, with the aim of predicting, if possible, the course of the infection.

Preferred mixtures in conformity with the invention are identified in the Table below:

TABLE

CHARACTERISTICS OF MIXTURES OF DNA OF HPVs UTILIZABLE FOR VIROLOGICAL DIAGNOSIS OF PAPILLOMAVIRUS INFECTIONS

| Designation of mixtures | Constitution[1] (type of HPV) | Diseases to be diagnosed |
| --- | --- | --- |
| 1 | 1, 2d, 4 | Epidermal and mucosal warts (in particular verruca and plantar warts) Differential diagnosis of epidermodysplasia veruciformis |
| 2 | 3, 10a, 10b, 28, 29 | Plane warts or intermediate epidermal or mucosal warts. Intra-epithelial neoplasias and epidermal cancers. Differential diagnosis of epidermodysplasia verruciformis. |
| 3 | 5, 17a, 24 | Epidermodysplasia verruciformis. Intra-epithelial neoplasias and epidermal cancers. |
| 4 | 5, 8, 12, 14a, 14b, 19, 20, 21, 22, 23, IP4 | Epidermodysplasia veruciformis. |
| 5 | 9, 15, 17a, 17b | Epidermodysplasia veruciformis. |
| 6 | 24 | Epidermodysplasia verruciformis. |
| 7 | 5, 8, 14b, 32, IP4 | Epidermal cancers of epidermodysplasia verruciformis. Intra-epithelial neoplasias and epidermal cancers. |
| 8 | 13, 31 | Oral focal epithelial hyperplasia; differential diagnosis of oral intra-epithelial neoplasias. |
| 9 | 32, IP4 | Intra-epithelial neoplasias and epidermal cancers. |
| 10 | 16, 18, IP2, IP5 | Genital neoplasias and cancers of uterine cervix |
| 11 | 6, 11, IP6 | Condylomas, papillomas |

The above table also shows the nature of the diseases likely to be diagnosed more especially by the use of the mixtures listed on the left hand side of the Table. A reminder is given that the restriction maps of the other DNA-HPVs identified in the preceding Table are presented in the FIGS. 1 to 9.

It is to be noted that HPV-IP5 and HPV-IP2 may be considered as particularly representative of probes which can be used for the detection of the risks of the development of cancer of the uterine cervix and HPV-IP6 as representative of probes which can be used for the detection of benign papilloma infections.

The DNA of HPV-IP6 may be associated with the DNA of HPV6 and/or HPV11.

Finally, the invention also relates to a mixture of all of the probes.

Similarly, the invention relates more especially to a cocktail of probes containing the DNA of the HPVs specific for genital cancers which contains:
HPV-IP2
HPV-IP5
HPV-IP6
HPV6
HPV11
HPV16
HPV18
HPV31
HPV35.

HPV-IP6 is representative of probes which can be used for the detection of benign papilloma infections.

The DNA of HPV-IP6 may be associated with the DNA of HPV6 and/or HPV11.

The invention thus also relates more particularly to diagnostic "kits" comprising at least 11 groups appearing in the groups numbered 1 to 11 in the Table under the heading "Designation of mixtures".

In the foregoing, the use as probes of cloned intact DNA-HPVs has been considered preeminently. The intact DNAs may, however, be replaced by cloned fragments of these different DNAs, particularly by genes E1 or L1 and by the genes E6-E7.

The basic principle of the in vitro detection of DNA-HPV naturally makes use of hybridizations performed under stringent or less stringent conditions. The procedure may be carried out as follows, provided it is understood that the diagnostic assays described are not considered as imposing limits on the conditions under which the probes or mixtures of probes according to the invention may be used.

The aim of the investigations using probes prepared from mixtures of cloned DNAs of HPVs is to demonstrate the presence of a HPV and to identify the type of HPV in a biopsy, in cells obtained by grattage of lesions or in biopsy sections fixed by the Carnoy mixture (ethanol:chloroform:acetic acid, 6:3:1), for example, and imbedded in paraffin. The investigation requires the prior extraction of the DNA of the samples according to methods, the principle of which is known and involves the analysis of this DNA by molecular hybridization experiments, carried out under stringent or less stringent conditions, by means of radioactive probes (labelled with $^{32}P$ or $^{35}S$) prepared from mixtures of DNA-HPVs. Each investigation usually requires the use of several mixtures of probes.

Several methods of hybridization may be used. For example, the method of dot blot hybridization may be used. This method involves the denaturation of the DNA and the depositing of aliquots of the DNA on membranes (nitrocellulose or Genescreenplus), the hybridization of each membrane under standard conditions with a mixture of probes and the detection of the radioactive hybrids by exposure of the membrane to a radiographic film. The method of Southern hybridization may also be used. This method consists of the electrophoretic separation of the DNA fragments produced by treatment of the DNA with restriction enzymes in an agarose gel, the transfer of the fragments to membranes (nitrocellulose, Genescreenplus) after alkaline denaturation and their hybridization under standard conditions with different mixtures of probes. The formation of radioactive hybrids is detected after exposure of the membrane to radiographic film.

Use may also be made of in situ hybridization, for example, on sections of tissues fixed by the Carnoy mixture and embedded in paraffin.

The radioactive probes are constituted either by the DNAs of HPVs labelled by the method of "nick-translation", or by RNAs prepared by transcribing the viral DNAs inserted into a vector of the pSP6 type, for example. The use of radioactive probes offers the advantage of high sensitivity but that does not exclude the use of non-radioactive probes, biotinylated probes for example, capable of being recognized by antibodies either labelled themselves or of being recognized by antibodies bearing a marker such as an enzyme, fluorescence label, etc.

The invention thus also relates to "kits" containing several probes of the type indicated above and consisting of:
separate samples of HPV-IP5 and HPV-IP6,
or these latter two probes taken together with others, in particular those defined above,
these "kits" being intended for in vitro diagnostic studies involving hybridization between the viral preparations obtained from patients and the various groups or mixtures.

It is obvious and also follows from the foregoing that the invention is in no way limited to those of its modes of application and realization which have been given particular consideration; on the contrary, it includes all possible variants; in particular, the reference in the claims to a designation DNA-HPV followed by a specific number corresponding to a DNA-HPV, the restriction map of which has been provided in the Figures, is to be understood as indicating that these claims cover all of the DNA-HPVs which have in common with this particular DNA-HPV properties allowing them to be classed as being of the same type, in accordance with the definition of the type given above and, with stronger reason, all of the DNA-HPVs which belong to the same subtype.

It will be noted that the recombinant DNAs designated below were deposited with the C.N.C.M. (Collection Nationale des Cultures de Micro-Organismes de l'INSTITUT PASTEUR de Paris 28 rue du Docteur Roux, 75724 Paris Cedex 15, France;) on Jan. 21st, 1986, under the numbers shown:
pSP65/IP5 (plasmid in *E. coli*): No. I-507
pSP64/IP6 (plasmid in *E. coli*): No. I-508

BIBLIOGRAPHIE (1) Dûrst, M. et al., 1983, Proc. Natl. Acad. Sci. U.S.A., 80:3812–3815. (lbis) Bospart M. et al., 1984, Embo J. 3=1151–1157
(2) Coggin, J. R., Jr. et al., 1979, Cancer Res., 39:545–546.
(3) Gissmann, L. et al., 1982, J. Virol. 44:393–400.
(4) Green, M. et al., 1982; Proc. Natl. Acad. Sci. U.S.A. 79:4437–4441.
(5) Heilman, C. A. et al., 1980, Virol. 36:395–407.
(6) Jablonska, S. et al., 1972, Cancer Res., 32:583–589.
(7) Jablonska, S. et al., 1982, Springer Semin. Immunopathol. 5:33–62.
(8) Kremsdorf, D. et al., 1982, J. Virol. 43:436–447.
(9) Kremsdorf. D. et al., 1983, J. Virol. 48:340–351.
(10) Lutzner, M. A. et al., 1978, Bull. Cancer, 65:169–182.
(11) Lutzner, M. A. et al., 1983, Lancet ii:422–424.
(12) Migozzi, M. et al., 1965, Bull. Soc. Franc. Derm. Syph. 72:747–748.
(13) Orth, G. et al., 1980, Cold Spring Harbor Conf. Cell Proliferation, 7:259–282.
(14) Orth, G. et al., 1981, J. Invest. Dermatol. 76:97–102.
(15) Orth, G. et al., 1979, Cancer Res. 39:1074–1082.
(16) Ostrow, R. S. et al, 1982, Proc. Natl. Acad. Sci. U.S.A., 79:1634–1638.
(17) Ostrow, R. S. et al., 1983, Ann. Acad. Dermatol. 8:398–404.
(18) Pfister, H. et al., 1983, Cancer Res. 43:1436–1441.
(19) Pfister, H. et al., 1983, J. Virol. 47:363–366.
(20) Pfister, H. et al., 1981, Int. J. Cancer, 27:645–650.
(21) Rueda, L. A. et al., 1976, Med. Cut. I.L.A. 2:113–136.

(22) Ruiter, M. et al. J. Invest. Dermatol., 47:247–252.
(23) Sutcliffe, J. G., 1978, Nucleic Acids Res. 5:2721–2728.
(24) Tsumori, T. et al., 1983, J. Gen. Virol. 64:967–969.

The following literature references must also be taken into account (some of the references are preceded by the designation of a particular HPV when the latter is being described for the first time by the authors concerned):

HPV18: BOSHART M. et al., 1984, EMBO J., 3:1151–1157,

HPV-IP2:
 BEAUDENON S. et al., 1986, Nature, 321:246,249,
 BEAUDENON S. et al., 1987, J. Inv. Dermatol., 88 N° 1,
 KAWASHIMA M. et al., 1986a, J. Virol., 57:688–692,
 KAWASHIMA M. et al., 1986b, Virology, 154:389–394, HPV6: DE VILLIERS E. M. et al., 1981, J. Virol., 40:932–935, HPV11: GISSMANN L. et al., 1982, J. Virol., 44:393–400, HPV31: LORINCZ A. et al., 1986a, J. Virol., 58:225–229, HPV35: LORINCZ A. et al., 1986b, Bambury report, 21:225–237, HPV16: DURST et al., 1983.

The designations of some of the HPV described in this application have been modified in the light of the international nomenclature now in force. In particular, the names of the isolates given on the right hand side of the following table (which are those used in the present text) henceforth bear the designations shown on the left:

HPV32 instead of HPV31 (BEAUDENON S. et al., 1987),

HPV34 instead of HPV32 (KAWASHIMA M. et al., 1986),

HPV33 instead of HPV-IP2 (BEAUDENON S. et al., 1986),

HPV36 instead of HPV-IP4 (KAWASHIMA M. et al., 1986),

HPV39 instead of HPV-IP5 (BEAUDENON S. et al., article in preparation),

HPV42 instead of HPV-IP6 (BEAUDENON S. et al., article in preparation).

We claim:

1. Isolated DNA of a human papillomavirus (HPV), wherein
 said DNA is about 7,000 to about 8,000 base pairs; and
 said DNA is obtained from a virus selected from the group of papillomaviruses consisting of HPV-IP5 and HPV-IP6.

2. A DNA according to claim 1, wherein said DNA encodes a gene of said HPV DNA, and wherein said gene is selected from the group of genes consisting of E1, E6-E7, L1, and L2.

3. An isolated DNA fragment, wherein said DNA fragment is obtained by treating HPV-IP5 DNA, or DNA complementary to HPV-IP5 DNA, with at least one restriction enzyme selected from the group consisting of EcoRI, PstI, HindII, PvuII, BamHI, HindIII, KpnI, AveI, and XbaI, and isolating said DNA fragment.

4. An isolated DNA fragment, wherein said DNA fragment is obtained by treating HPV-IP6 DNA, or DNA complementary to HPV-IP6 DNA, with at least one restriction enzyme selected from the group consisting of EcoRI, PstI, HindII, PvuII, BamHI, HindIII, KpnI, AccI, BglII, SepI, EcoRV, and XbaI, and isolating said DNA fragment.

5. Recombinant human papillomavirus (HPV) DNA consisting of DNA according to claim 1.

6. A probe for the detection of human papillomavirus (HPV), said probe consisting of the DNA of claim 1.

7. The plasmid pSP65/IP5.

8. The plasmid pSP64/IP6.

* * * * *